United States Patent [19]

James et al.

[11] Patent Number: 5,055,429
[45] Date of Patent: * Oct. 8, 1991

[54] POROUS INORGANIC MATERIAL

[75] Inventors: Roger James, St. Austell, Cornwall, United Kingdom; Alan J. Brown, Tennille, Ga.

[73] Assignee: ECC International Limited, United Kingdom

[*] Notice: The portion of the term of this patent subsequent to Jun. 26, 2007 has been disclaimed.

[21] Appl. No.: 275,429

[22] Filed: Nov. 22, 1988

[30] Foreign Application Priority Data

Nov. 27, 1987 [GB] United Kingdom ............... 8727819
Dec. 10, 1987 [GB] United Kingdom ............... 8728877

[51] Int. Cl.$^5$ ............................................. C04B 38/00
[52] U.S. Cl. .................................... 501/;80; 501/129; 264/42; 264/48; 264/49
[58] Field of Search .......................... 501/80, 128, 129; 264/42, 48, 49

[56] References Cited

U.S. PATENT DOCUMENTS 3,526,602  9/1970  Kobayashi et al. .
3,855,172 12/1974  Iler et al. .
4,826,789  5/1989  Jones et al. ........................... 501/80
4,826,790  5/1989  Jones et al. ........................... 501/80
4,937,209  6/1990  Jones et al. .
4,937,210  6/1990  Jones et al. .

FOREIGN PATENT DOCUMENTS

56785/86 11/1986 Australia .
1555230 11/1979 United Kingdom .
2153807  8/1985 United Kingdom .

Primary Examiner—William R. Dixon, Jr.
Assistant Examiner—Chris Gallo
Attorney, Agent, or Firm—Klauber & Jackson

[57] ABSTRACT

There is disclosed a porous inorganic material, suitable for use as a support material for biological macromolecules, comprising substantially spherical particles of an aluminosilicate ceramic material, any internal cavities present in a particle occupying no more than 10% of the volume of the particle, each particle having a diameter in the range of from 5 micrometers to 5 millimeters and consisting predominantly of an open three-dimensional matrix of needles of the ceramic material each of which needles has a length in the range of from 2 to 20 micrometers and a width in the range of from about 0.2 to 2 micrometers, the ceramic needles defining between them interconnecting pores of width of from 0.1 to 5 micrometers. Also disclosed is a method of preparing such a porous inorganic material.

15 Claims, 8 Drawing Sheets

POROUS INORGANIC MATERIAL

This invention relates to a porous inorganic material and to a process for preparing such a material. The porous material of the present invention is ideally suited for immobilising biochemical macromolecules such as enzymes or other proteins.

Figure 1:
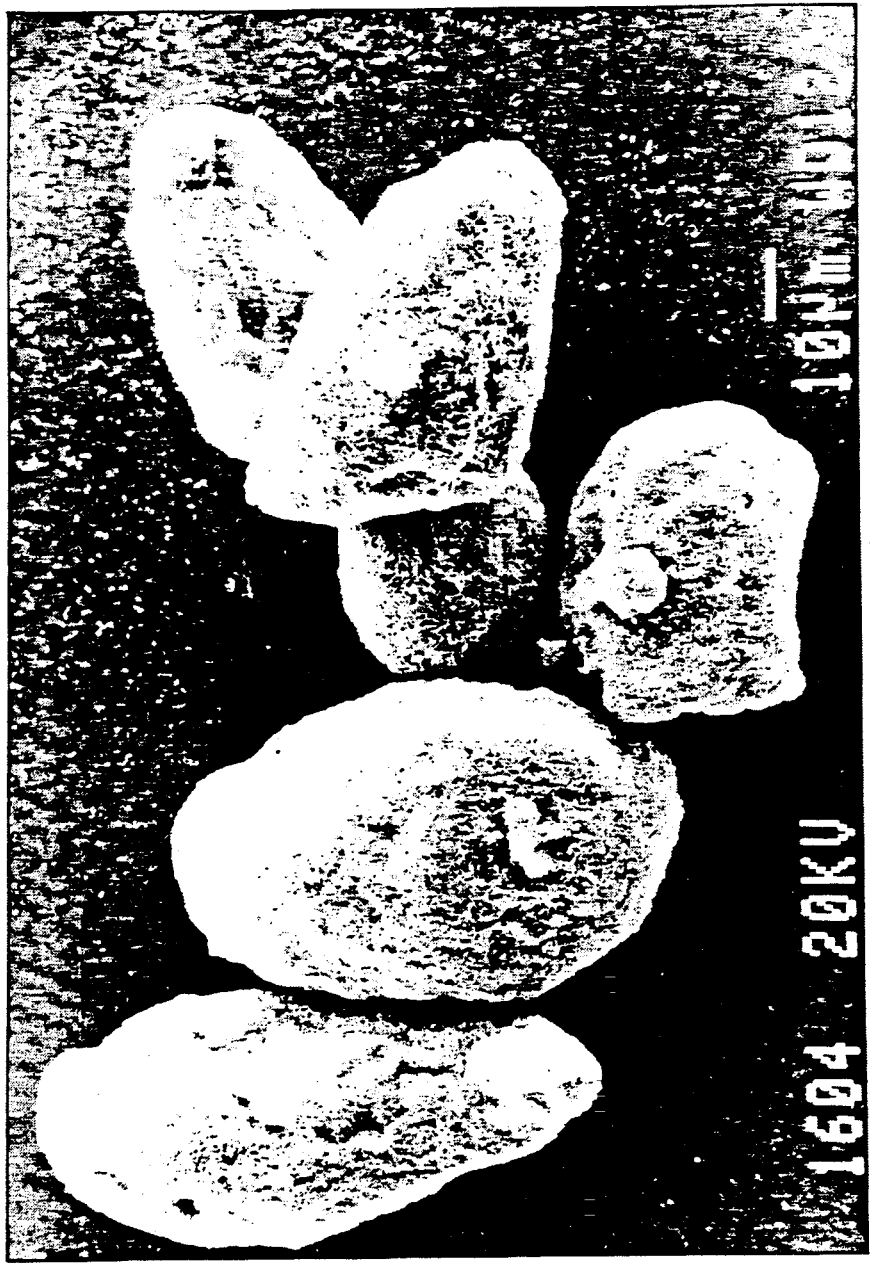

GB-2153807A discloses a particulate porous material in which substantially all the particles of the material are not smaller than 5 micrometres and not larger than 1 millimetre in diameter and wherein each particle consists predominantly of an open, three-dimensional matrix of crystals of mullite which define between them interconnecting pores having a width in the range of from 5 nanometers to about 2 micrometres. Processes for producing such particles are also described. Generally, the particles produced by the processes described are irregular and "chunky" in appearance (as shown in FIG. 1 of this application), such particles being produced by high temperature calcination of a mass of kaolin clay followed by leaching with an alkali. Employing the process described in GB-2153807A results in particles which have a shape which is irregular. In addition, GB2153807A discloses a process in which a kaolin clay suspension comprising 62% by weight of dry kaolin is spray dried to form hollow spherical particles which are subsequently calcined and leached. The particles produced by the processes disclosed in GB-2153807A suffer from at least two disadvantages. Firstly, the irregular-shaped or chunky particles are not particularly suitable as a packing material for a column, spherical particles being preferred, and secondly the hollow spherical particles produced by the process including a spray drying step are inefficient as a packing material or as a support for biological macromolecules such as proteins since the internal cavity can perform no supporting function.

It is, therefore, an object of this invention to provide a porous material suitable for immobilising biological macromolecules.

EP-0130734 and EP-0187007 each relate to the production of porous mullite for use as precious metal catalyst supports.

According to a first aspect of the present invention, there is provided a porous inorganic material, suitable for use as a support material for biological macromolecules, comprising substantially spherical particles of an aluminosilicate ceramic material, any internal cavities present in a particle occupying no more than 10% of the volume of the particle, each particle having a diameter in the range of from 5 micrometres to 5 millimetres and consisting predominantly of an open three-dimensional matrix of needles of the ceramic material each of which needles has a length in the range of from 2 to 20 micrometres and a width in the range of from about 0.2 to 2 micrometres, the ceramic needles defining between them interconnecting pores of width of from 0.1 to 5 micrometres.

Preferably, any internal cavities present in a particle occupy no more than 5% of the volume of the particle. As used herein, an "internal cavity" is considered to be a void having a diameter greater than about 10% of the diameter of the microsphere.

Preferably, the aluminosilicate ceramic material is mullite.

According to a second aspect of the present invention there is provided a method of preparing a porous inorganic material, which method comprises:

a) preparing an aqueous suspension of a porous inorganic material comprising aggregates of platelets of an aluminosilicate material having an $SiO_2:Al_2O_3$ molar ratio of at least 0.75:1, said suspension containing from 20% to 40% on a dry weight basis of an inorganic material and up to 20% by weight, based on the weight of dry inorganic material, of a hydrophilic organic polymer;

b) spray-drying the suspension to form substantially spherical microspheres, any internal cavity in a microsphere occupying no more than 10% of the volume of the microsphere;

c) calcining the spray-dried microspheres at a temperature in the range of from 1300° C. to 1800° C. for at least one hour;

d) treating the calcined microspheres with a concentrated aqueous solution of an alkali metal hydroxide at a temperature of at least 50° C. whereby the silica is removed to leave ceramic crystals which define between them interconnecting pores;

e) washing the alkali metal hydroxide treated microspheres until the washing medium is substantially free of silicate and alkali metal ions; and f) dewatering and drying the washed product obtained in step e) to obtain substantially spherical microspheres, any internal cavities present in a microsphere occupying no more than 10% of the volume of the microsphere.

According to a third aspect of the present invention there is provided a packed column in which the packing material is a particulate porous material according to the first aspect of this invention.

According to a fourth aspect of this invention there is provided a method of supporting biological macromolecules, which comprises adsorbing said macromolecules into the interconnecting pore structure of a porous inorganic material in accordance with the first aspect of this invention.

The hydrophilic organic polymer may be, for example, a water dispersible synthetic polymer such as poly(vinyl acetate) or poly(vinyl alcohol), or a water dispersible natural polymer which may be, for example, carbohydrate-based, such as dextran, starch, agar, guar gum, hydroxyethyl cellulose or sodium carboxymethyl cellulose, or protein-based, for example casein or gelatin. This hydrophilic polymer is preferably used in an amount of at least 1% by weight, based on the weight of dry inorganic material. The hydrophilic polymer regulates the size of droplets formed in spray-drying by increasing the viscosity of the suspension to mimic higher concentrations of platelets. However, although viscosifying, it does not interfere with the spray-drying.

In step b) of the process of this invention, the suspension from step a) is preferably spray-dried by spraying the suspension into a suitable vessel in which hot gases are circulating.

The aluminosilicate starting material may be chosen from the following: kyanite, sillimanite and andalusite, all of which can be represented by the chemical formula $Al_2O_3 \cdot SiO_2$, dumortierite which can be represented by the chemical formula $8Al_2O_3 \cdot B_2O_3 \cdot 6SiO_2 \cdot H_2O$; clay minerals of the kandite group which can be represented by the chemical formula $Al_2O_3 \cdot 2SiO_2 \cdot 2H_2O$ and pyrophillite which can be represented by the chemical formula $Al_2O_3 \cdot 4SiO_2 \cdot H_2O$. Other possible aluminosilicate starting materials include topaz, pinite, illite and clay minerals of the smectite class. It is also possible to use as the aluminosilicate starting material a mixture of an alumina-rich material and a silica-rich material, or a mixture of substantially pure alumina and silica provided that the molar ratio $SiO_2:Al_2O_3$ is at least 0.75:1 and preferably at least 1:1 in each case. Especially suitable are clay minerals of the kandite class, namely kaolinite, dickite, nacrite and halloysite, and in particular kaolin clay which consists predominantly of kaolin.

Alternatively the starting material may be a magnesium aluminium silicate such as talc. In this case, after the material has been subjected to steps a) to f) above, the product will consist of microspheras of cordierite of chemical formula $2MgO.2Al_2O_3.5SiO_2$.

Most preferably, the aluminosilicate starting material in step a) of the process of the present invention is kaolin or metakaolin. The calcined, leached microspheres will then be formed of mullite crystals.

It is an important feature of the process of this invention that the clay based material which is used to make the aqueous suspension in step a) comprises aggregates of relatively small platelets of the aluminosilicate material. Without wishing to be bound by theory, it is believed that the droplets of suspension in the spray dryer chamber form an initial outer skin which is pervious to vapour. As a result steam formed in the interior of the droplet is released relatively slowly and in a controlled manner through the outer skin, with the result that the spray dried product comprises substantially spherical microspheres which are free from any internal cavity or have one or more internal cavities which occupy in total no more than 5% of the volume of the microsphere. In the aggregates, the platelets are randomly arranged; thus, in the droplet formed in the spray dryer, the platelets cannot align in the plane of the outer skin of the droplet to create a substantially impervious skin. If such was the case, and the platelets could align-as is the case with an unaggregated aluminosilicate material such as, for example, hydrous kaolin clay-any steam formed in the droplet would tend to burst through the wall leaving a relatively large internal cavity and an aperture in the wall of the microsphere.

The porous inorganic material used in step a) of the process in accordance with this invention may be formed either by sintering together the platelets of a finely divided kaolin clay product by calcination at a relatively low temperature or by chemical aggregation of the platelets.

A process for forming a suitable porous inorganic material by calcination is described in US-A-4381948. A relatively fine raw kaolin is plunged in water to form a dispersion of the same. The resultant aqueous suspension is subjected to a particle size distribution such that substantially all particles are smaller than 2 micrometres e.s.d., preferably substantially all particles are smaller than 1 micrometre e.s.d. The suspension of the fine product is dried to produce a substantially moisture-free clay which is then thoroughly pulverised to break up agglomerates. This material is then used as a feed to a calciner and calcined under controlled conditions at a temperature in the range of from 900° C. to 1100° C., the product being a porous metakaolin comprising aggregates of substantially hexagonal platelets the shape and size of which are dictated by the nature of the raw kaolin.

A suitable porous inorganic material may alternatively be produced by the processes described in EP-0274429 and EP-0274430. Thus, in the process described in EP-0274430, a raw kaolin having a particle size distribution such that 70 to 100% by weight of the particles are smaller than 1 micrometre e.s.d. is dried to remove substantially all of its physically bound water while removing substantially none of its chemically bound water, and is subsequently treated with from 10 to 40 lb/ton (5.20 Kg/tonne) of a chloride of silicon, titanium or aluminium. It is also advantageous to mix with the kaolin feed from 0.5 to 12% by weight, based on the weight of kaolin, of a particulate alkaline earth carbonate or hydroxide, or lithium carbonate. Preferably, from 4 to 8 kg/tonne of ammonia, urea or an organic amine is added to the mixture of kaolin and chloride. The product of this process is a porous inorganic material comprising aggregates of kaolin clay platelets.

The porosity of the inorganic material produced by the process of the present invention may be increased by treating the product of step e) or step f) above with an aqueous solution containing from 2% to 30% by weight of hydrofluoric acid. If the concentration of the solution of hydrofluoric acid is greater than about 30% by weight, the porous mullite matrix tends to disintegrate completely.

The porous inorganic material of the invention may be used as a packing medium for a column. It has good mechanical properties in service and can be used for bio-filtration, gel filtration chromatography, affinity chromatography, ion exchange chromatography or for enzyme or other protein immobilization. When the material according to the invention is used as a support for a bio-catalyst, such as an enzyme or other protein, nutrients held in suspension in a liquid are able to diffuse freely to the bio-catalyst immobilized within the material and products are able to diffuse freely away.

The microspheres which are the product of step b) of the process of the present invention may, if desired, be formed into large shaped bodies, each body comprising a plurality of individual microspheres. The shaped bodies may be formed by a granulation process, for example in a pan pelletiser, or by subjecting the microspheres to light pressure in a mould of appropriate dimensions, for example a tablet press. The shaped bodies are then calcined and further treated according to steps c) to f) described above.

The porous inorganic material is readily coated with a reactive layer for the purposes of affinity or ion exchange chromatography or for biochemical separations. Examples of materials which can be coated on to the particulate porous material to form reactive layers include polyacidic organic bases such as polyethyleneimines, which will form bonds directly with the surface of the mullite crystals Such polyacidic organic bases also possess both hydrophobic and hydrophilic groups and have anion exchange properties which are useful in biological applications such as treating proteins. Other materials which can be coated directly on to the mullite crystals include thermoplastic materials such as polystyrene and polysaccharides. An example of a substituted polysaccharide material which has been found to form a useful reactive layer is "DEAE Dextran" which is a dextran substituted with pendant diethylamine ethyl groups; this provides a hydrophilic organic layer with anion exchange properties. The surface of the particulate porous material may be rendered hydrophobic, and be given an overall positive charge, by applying a coating of a quaternary ammonium compound which has at least one hydrocarbon radical with from 10 to 24 carbon atoms.

Some materials can only be used to form reactive layers after the mullite crystals have first been coated with a bonding agent. Suitable bonding agents are substituted silanes, especially those comprising at least one hydroxy, hydroxyalkyl or alkoxy group for bonding with hydroxyl groups on the surface of the mullite crystals and at least one aminoalkyl, diazo or haloalkyl group for bonding with the material of the desired layer. An example of a suitable substituted silane is 3-aminopropyltriethoxysilane with the substituted silane including nucleic acid bases, such as adenine which is very useful for the concentration and separation of nucleic acids, and polysuccinimide which is very suitable for affinity chromatography and for immobilizing enzymes.

The invention will now be illustrated by the following Examples:

EXAMPLE 1

A sample of a raw kaolin clay from Georgia, U.S.A. having a particle size distribution such that 80% by weight consisted of particles having an equivalent spherical diameter (e.s.d.) smaller than 2 micrometres was mixed with sufficient water to form a suspension containing 60% by weight of solids and with 0.18% by weight, based on the weight of dry kaolin, of a sodium polyacrylate dispersing agent having a number average molecular weight of 1680. The 60% by weight solids suspension was then diluted with water to 15% by weight solids and passed through a sieve of nominal aperture 44 micrometres to remove particles of grit. The degritted suspension was subjected to a particle size separation in a centrifuge to yield a fine product which had a particular size distribution such that 100% by weight consisted of particles having an e.s.d. smaller than 1 micrometre. The suspension of the fine products was flocculated, dewatered by filtration and the filter cake redispersed by mixing with sodium polyacrylate dispersing agent dissolved in a small quantity of water to form a suspension containing about 60% by weight of dry kaolin.

This suspension was spray dried to form microspheres of substantially bone dry kaolin which were pulverised in a laboratory hammer mill to liberate substantially completely the kaolin clay platelets. The pulverised product was then calcined in a muffle furnace for 30 minutes under conditions such that all of the clay was brought to a temperature of at least 900° C. while substantially none of the clay was heated to a temperature in excess of 1100° C. This procedure produces metakaolin. The calcined product was then pulverised in the laboratory hammer mill in order to break up any large agglomerates, i.e. greater than about 10 micrometres, while not impairing the internal structure of the fundamental discrete aggregates which define the calcined product.

Figure 2:
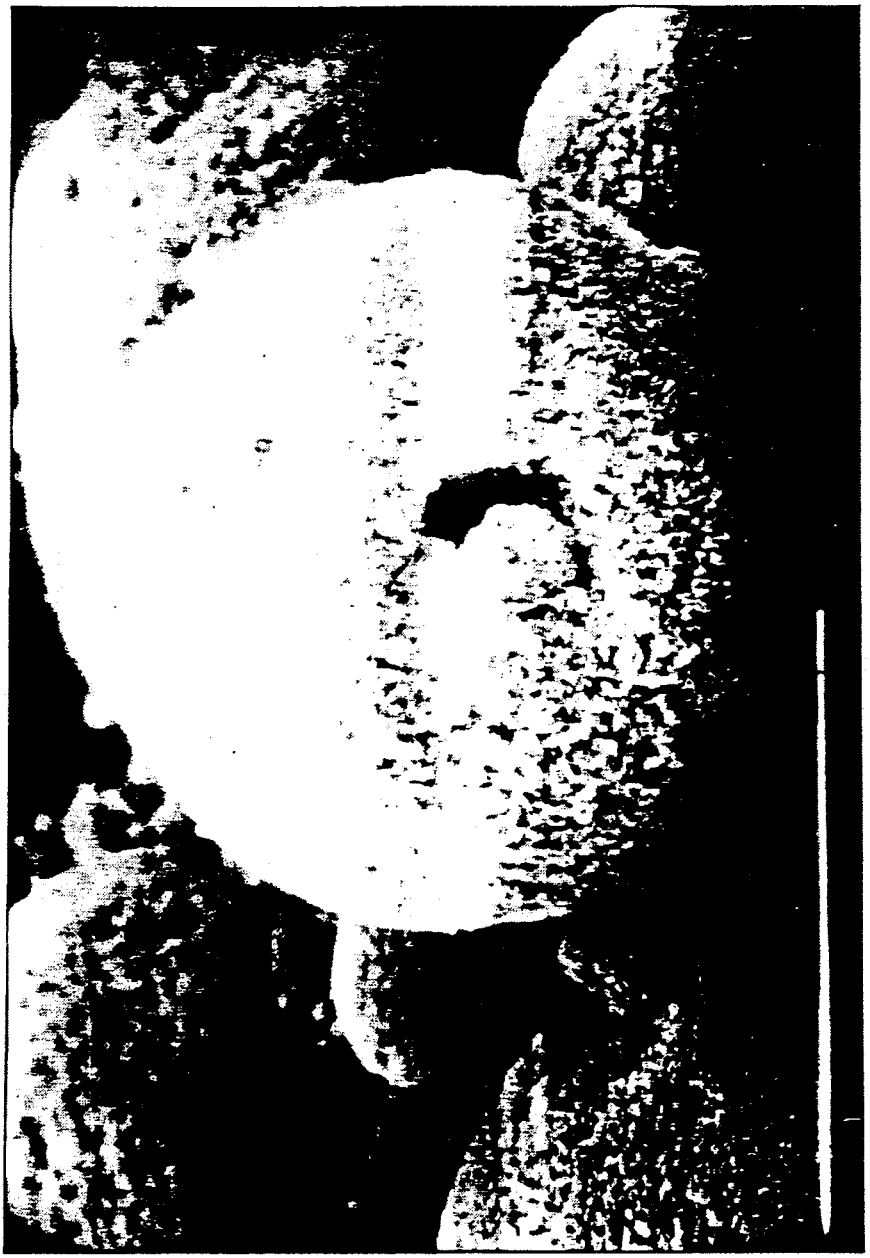
Figure 3:

The pulverulent calcined product comprising aggregates of metakaolin platelets was mixed with water to form a suspension containing 35% by weight of dry solids and there was added to the suspension 10% by weight, based on the weight of the dry calcined metakaolin, of sodium carboxymethyl cellulose as a viscosifying agent. The resultant mixture was spray dried and the spray dried product consisted of substantially spherical solid particles with, at most, only a small internal cavity (see FIG. 2). An enlarged view of the surface of a particle is shown in FIG. 3.

Figure 4:
Figure 5:

The spray dried particles were calcined in a tunnel kiln under conditions such that they were exposed to a temperature of 1500° C. for 8 hours. The calcined product was then boiled with 3M sodium hydroxide solution for 1 hour to dissolve the silica phase leaving a rigid intermeshing matrix of mullite needles. The liquor was removed by filtration and the particulate product was washed with hot water, the washings also being removed by filtration until the washings were found to be substantially free of sodium and silicate ions. The washed material was then dried in an oven at 60° C. and the dry cake lightly milled to break up any agglomerates. The product (FIGS. 4 and 5) consisted of substantially spherical particles of overall diameter about 50 micrometres, each particle comprising a three-dimensional network of mullite needles of length about 2 to 5 micrometres and width of about 0.2 to 0.5 micrometres, defining between them interconnecting pores of width about 0.2 to 0.5 micrometre.

EXAMPLE 2

Figure 6:
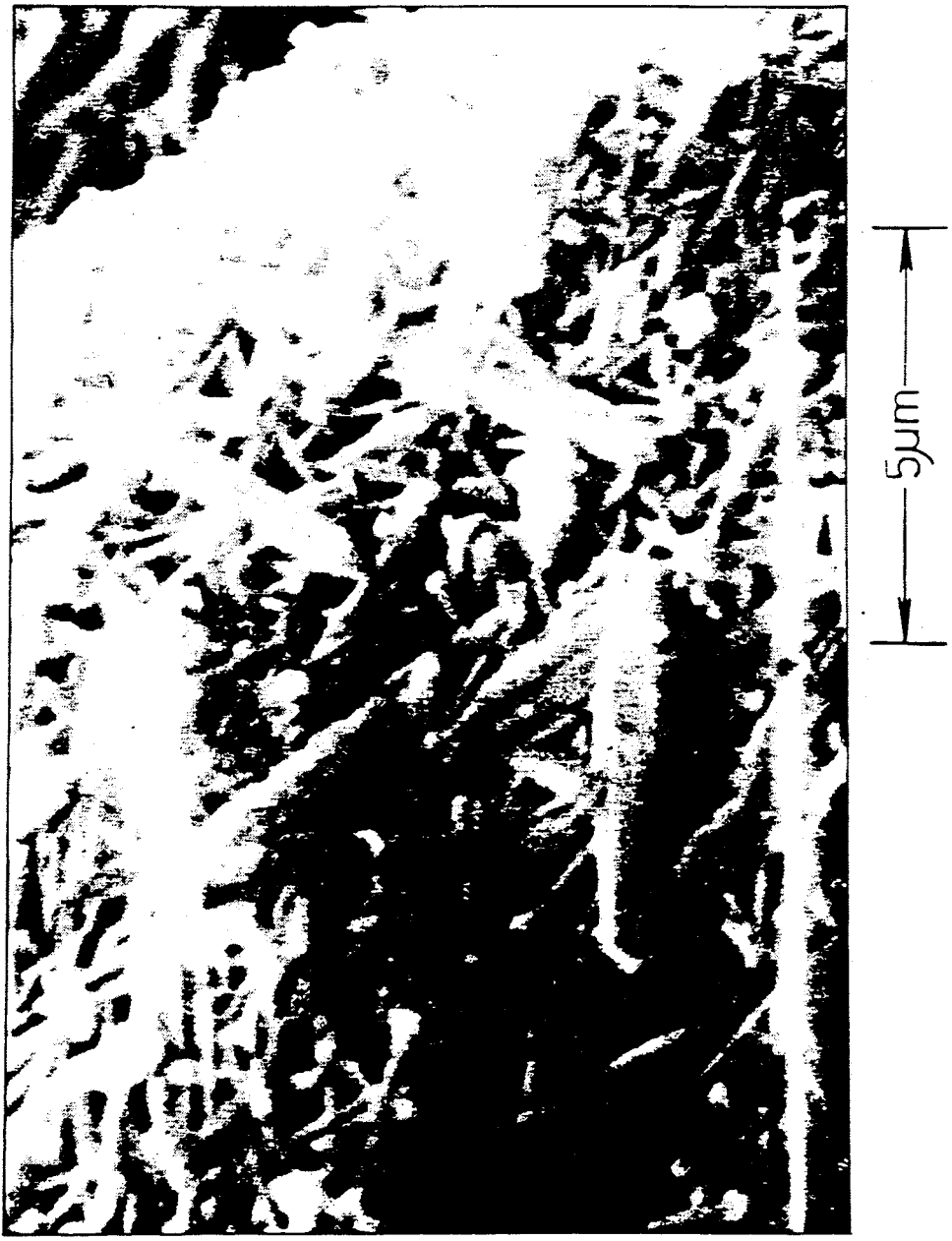

The mechanical strength of the product of Example 1 was tested by packing a high performance liquid chromatography column with the product under a pressure of 8000 psig (55 MPa). The column had a diameter of 7 mm and length of 250 mm, and was fitted at its lower end with a fritted stainless steel disc of pore width 2 micrometres. A reservoir containing a slurry of the product was connected by means of a pressure coupling to the column and the slurry was forced into the column under pneumatic pressure. A buffer solution comprising 0.25M $Na_2HPO_4$, 0.1M NaCl and sufficient NaOH solution to adjust the pH to 6.8 was passed through each column at a series of different flow rates and the back pressure caused by the packing at each flow rate was measured. The results are shown graphically in FIG. 6. The fact that the back pressure increased only linearly with flow rate indicates that there has been no significant breaking down of the particles under a crushing pressure of 55 MPa to yield fine particles having diameters smaller than about 20 microns which would be detected by blocking the pores of the fitted stainless steel disc.

EXAMPLE 3

A porous inorganic material was prepared using the same starting materials and following the same method as described in Example 1, except that, immediately before the step of calcining in the tunnel kiln, the spray dried particles were granulated by tumbling in a pan pelletiser with a 10% by weight aqueous solution of a quaternised polyacrylamide flocculant to produce granules of diameter about 2 to 3 millimetres. Samples of these granules were then calcined in the tunnel kiln at different temperatures for different lengths of time, and in each case the calcined granules were leached with 3M sodium hydroxide solution, washed, dewatered and dried as described in Example 1.

The crushing strength of the granules was determined by resting large steel weights in the range 0.5 to 20 KJg on single granules and observing the greatest weight which the granule could support without being crushed.

The results obtained are set forth in Table 1:

TABLE I

| Calcining temp (°C.) | Calcining time (hours) | Crush strength (kg) |
| --- | --- | --- |
| 1050 | 1 | 0.5 |
| 1100 | 1 | 0.75 |
| 1150 | 1 | 1.0 |
| 1200 | 1 | 5.0 |
| 1250 | 1 | 7.5 |
| 1250 | 5 | 8.0 |
| 1250 | 9 | 10.0 |
| 1500 | 6 | 15.0 |

These results show that granules which have been calcined at 1250° C. or below have a relatively low crush strength, and that a calcination temperature of about 1500° C. is required if the porous inorganic particles are to be strong enough to withstand service as a packing medium in a commercial-scale column.

EXAMPLE 4

The degree of adsorption of protein to a porous inorganic material in accordance with the invention was investigated by adding 1g of the porous material to 15 ml of an aqueous solution containing 100 ppm of yoglobin and subjecting the mixture to mild agitation in the form of a gentle tumbling action for 18 hours to allow equilibrium to be reached. The mixture was then allowed to stand for 5 hours and centrifuged for 5 minutes at 3000 rpm to separate the particulate material from the solution of unabsorbed protein. The protein content of the initial solution and of the solution of unabsorbed protein separated by the centrifuge was determined by ultraviolet spectrophotometry and the difference between the two measurements gave a measure of the quantity of myoglobin in milligrams which was adsorbed by 1gram of the particulate material. The specific surface area of the porous material was also determined by the B.E.T. nitrogen adsorption method.

The porous inorganic materials investigated in the above manner were respectively the product of the tunnel kiln in Example 1, without and with subsequent treatment in 3M sodium hydroxide solution and the tunnel kiln calcined, sodium hydroxide treated product of Example 1, coated with varying amounts of gammaaminopropyltriethoxysilane. The silane coated materials were tested for loss on ignition by determining their loss of weight after heating to 1000° C. for 1 hour.

The results obtained are set forth in Table II:

TABLE II

| Material | % by wt. of silane | Specific surface area ($m^2g^{-1}$) | % loss on ignition | Weight of Protein adsorbed ($mg \cdot g^{-1}$) |
| --- | --- | --- | --- | --- |
| Ex. 1 not NaOH treated | 0 | 0.3 | — | 0.41 |
| Ex. 1 NaOH treated | 0 | 1.5 | — | 0.95 |
| Ex. 1 NaOH treated | 0.5 | 0.7 | 0.05 | 1.3 |
| Ex. 1 NaOH treated | 1.0 | 1.5 | 0.09 | 1.3 |
| Ex. 1 NaOH treated | 1.5 | 1.6 | 0.44 | 1.2 |
| Ex. 1 NaOH treated | 2.0 | 1.0 | 0.74 | 1.9 |

These results show that greater quantities of protein can be adsorbed if the porous inorganic material is coated with a substituted silane.

EXAMPLE 5

The porous inorganic product of Example 1 was mixed with water to form a suspension containing 10% by weight of dry solids The suspension was then mixed at a temperature of 60° C. with sufficient amount of a solution containing 10% by weight of the quaternary ammonium compound, dimethyl di(hydrogenated tallow) ammonium hydrochloride (2M2HT) to provide 8 milliequivalents of 2M2HT per 100 g of dry inorganic material. The mixture was stirred at a temperature of 60° C. for half an hour after which the suspension was filtered and the cake washed with water and dried.

The coated inorganic material thus prepared was tested for its protein adsorption capacity by the method described in Example 4 above. The specific surface area of the coated material was found to be 1.5 $m^2g^{-1}$, its loss on ignition at 1000° C. for 1 hour was 0.8% by weight and the weight of myoglobin adsorbed was 2.5 mg. $g^{-1}$.

EXAMPLE 6

Figure 7:
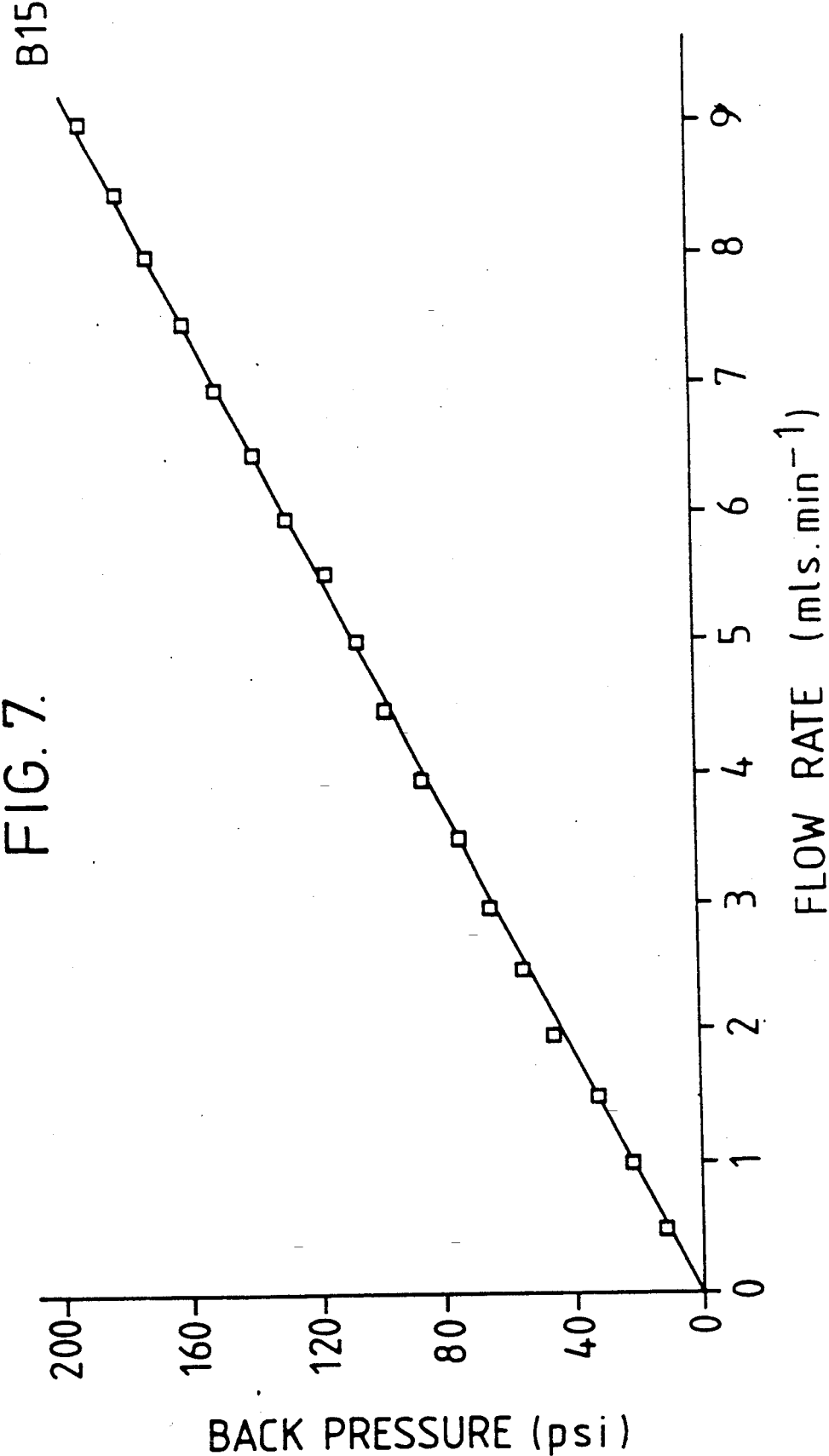

The porous inorganic product of Example 1 was further treated by mixing an aqueous suspension containing 10% by weight of the porous product with an aqueous solution containing 5% by weight of hydrogen fluoride for half an hour at room temperature. The treated inorganic product was separated by filtration, washed with water, again separated by filtration and dried and the final product (see FIG. 7) was found to have a specific surface area as measured by the BET method of 5 $m^2g^{-1}$ which is a further improvement in the surface available for adsorption of biochemical macromolecules such as enzymes or other proteins.

The mechanical strength of the inorganic material was found to be substantially unchanged by the treatment with dilute hydrofluoric acid. The above experiment was repeated except that a 40% by weight solution of hydrogen fluoride was substituted for the 5% by weight solution. It was found that the three dimensional mullite matrix collapsed completely leaving only single mullite needles.

The capacity of the product treated with dilute hydrofluoric acid as described above to adsorb enzymes was investigated by first activating the surface of the porous material with glutaraldehyde. For 1 gram of the porous material there was added 25ml of 2.5% by weight glutaraldehyde solution in 0.05M potassium dihydrogen orthophosphate buffer at pH 7.0. The porous material was allowed to remain in contact with the activating solution for 60 minutes, after which it was separated by filtration, washed thoroughly with more of the same buffer solution and used while still damp. The absorption of the enzymes urease and trypsin in potassium dihydrogen orthophosphate buffer solutions of varying molarity was measured by shaking 100 mg of the activated porous material with 1 mg of the enzyme in 1 ml of the buffer of appropriate molarity for 60 minutes, separating the porous mixture from the liquor by centrifuging and determining the amount of enzyme left in solution by ultra-violet spectrophotometry at 280 nm.

For each buffer solution the experiment described above was repeated using 100 mg of unactivated porous material in place of the activated porous material and the amount of enzyme adsorbed on to the activated porous material was found by difference.

Figure 8:
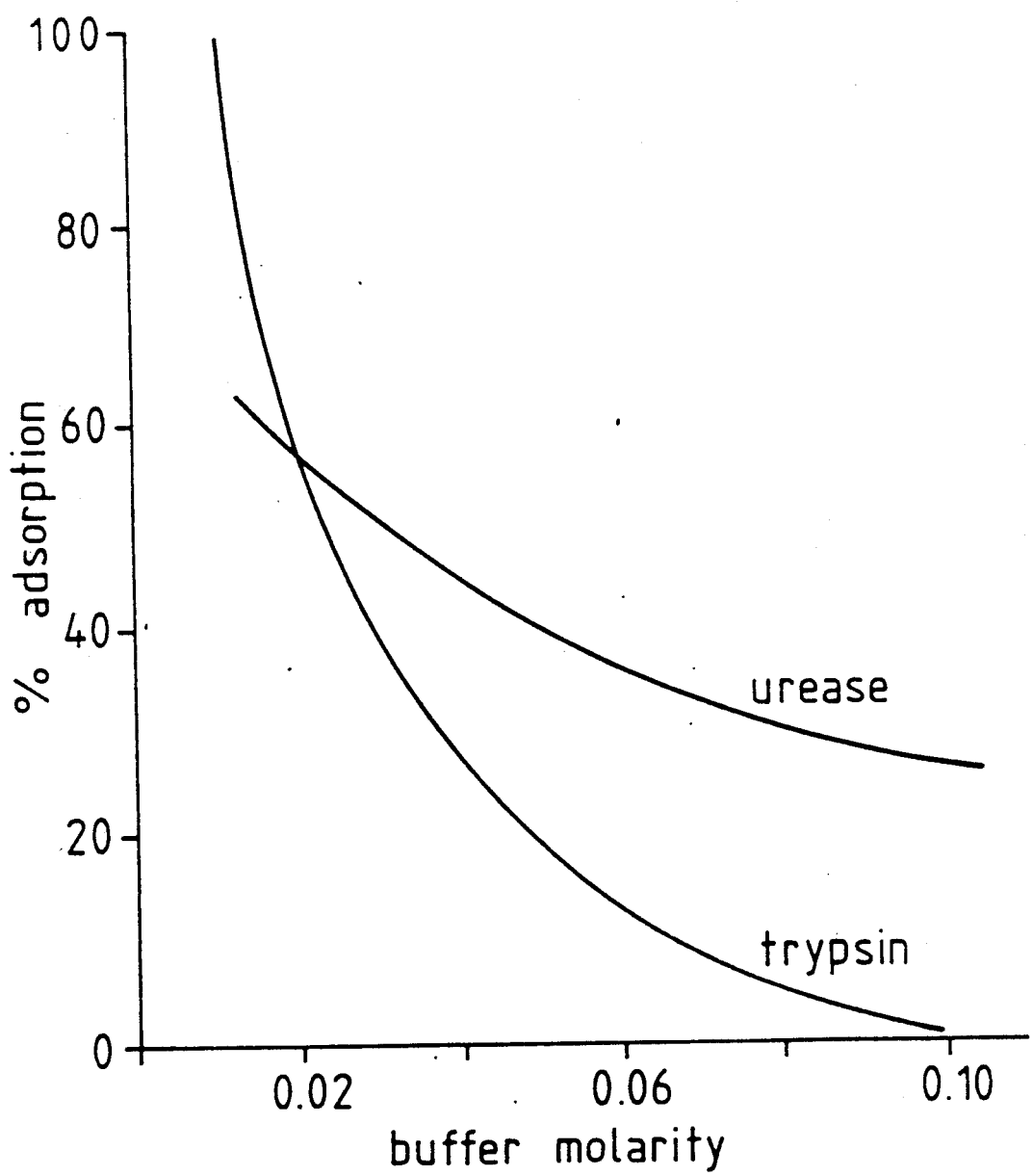

The results are shown graphically in FIG. 8.

A further experiment, in which the decomposition of urea in a 0.01M phosphate buffer by urease immobilized on the activated porous material was assessed spectrophotometrically, indicated that the activity of urease on the surface of the activated material was about 38%.

We claim:

1. A method of preparing a porous inorganic material, which method comprises:
   a) preparing an aqueous suspension of a porous inorganic material comprising aggregates of platelets of an aluminosilicate material having an $SiO_2:Al_2O_3$ molar ratio of at least 0.75:1, said suspension containing from 20% to 40% on a dry weight basis of an inorganic material and up to 20% by weight, based on the weight of dry inorganic material, of a hydrophilic organic polymer;
   b) spray-drying the suspension to form substantially spherical microspheres, any internal cavities in a microsphere occupying no more than 10% of the volume of the microsphere;
   c) calcining the spray-dried microspheres at a temperature in the range of from 1300° C. to 1800° C. for at least one hour;
   d) treating the calcined microspheres with a concentrated aqueous solution of an alkali metal hydroxide at a temperature of at least 50° C. whereby the silica is removed to leave ceramic crystals which define between them interconnecting pores;
   e) washing the alkali metal hydroxide treated microspheres until the washing medium is substantially free of silicate and alkali metal ions; and
   f) dewatering and drying the washed product obtained in step e) to obtain substantially spherical microspheres, any internal cavities in a microsphere occupying no more than 10% of the volume of the microsphere.

2. A method according to claim 1, wherein any internal cavities in a microsphere occupy no more than 5% of the volume of the microsphere.

3. A method according to claim 1, wherein the aluminosilicate material used in step a) is a kaolin or metakaolin and the spherical microspheres comprise mullite crystals.

4. A method according to claim 3, wherein the porous inorganic material used in step a) is formed by sintering together the platelets of a finely divided kaolin clay by calcination at a relatively low temperature.

5. A method according to claim 4, wherein the platelets of finely divided kaolin clay are sintered together by calcination at a temperature no greater than 1100° C.

6. A method according to claim 3, wherein the porous inorganic material used in step a) is formed by chemical aggregation of the platelets of a finely divided kaolin clay.

7. A method according to claim 1, further comprising the step of treating the product of step e) or f) with an aqueous solution containing from 2% to 30% by weight of hydrofluoric acid.

8. A method according to claim 1, wherein the hydrophilic organic polymer is used in an amount of at least 1% by weight, based on the weight of dry inorganic material.

9. A method according to claim 1, wherein the platelets in step (a) are substantially hexagonal.

10. A porous inorganic material, suitable for use as a support material for biological macromolecules, comprising substantially spherical particles of an aluminosilicate ceramic material, any internal cavities present in a particle occupying no more than 10% of the volume of the particle, each particle having a diameter in the range of from 5 micrometres to 5 millimetres and consisting predominantly of an open three-dimensional matrix of needles of the ceramic material each of which needles has a length in the range of from 2 to 20 micrometres and a width in the range of from about 0.2 to 2 micrometres, the ceramic needles defining between them interconnecting pores of width of from 0.1 to 5 micrometres.

11. A porous inorganic material according to claim 10, wherein any internal cavities present in a particle occupy no more than 5% of the volume of the particle.

12. A porous inorganic material according to claim 10, wherein the aluminosilicate ceramic material is mullite.

13. A porous inorganic material as claimed in claim 10, wherein the particles are coated with a reactive layer.

14. A porous inorganic material as claimed in claim 13, wherein said reactive layer is an organic material.

15. A packed column in which the packing material is a particulate porous material comprising substantially spherical particles of an aluminosilicate ceramic material, any internal cavities present in a particle occupying no more than 10% of the volume of the particle, each particle having a diameter in the range of from 5 micrometres to 5 millimetres and consisting predominantly of an open three-dimensional matrix of needles of the ceramic material each of which needles has a length in the range of from 2 to 20 micrometres and a width in the range of from about 0.2 to 2 micrometres, the ceramic needles defining between them interconnecting pores of width of from 0.1 to 5 micrometres.

* * * * *